United States Patent [19]

Murel

[11] Patent Number: 4,925,545
[45] Date of Patent: May 15, 1990

[54] METHOD OF GENERATING PH FUNCTIONS IN ELECTROPHORESIS AND ISOELECTRIC FOCUSING

[75] Inventor: Andrew Murel, St. Louis, Mo.

[73] Assignee: Amest, Inc., St. Louis, Mo.

[21] Appl. No.: 304,429

[22] Filed: Jan. 31, 1989

[51] Int. Cl.$^5$ .................... B01D 57/02; G01N 27/28
[52] U.S. Cl. ........................... 204/182.9; 204/183.2; 204/299 R
[58] Field of Search ............. 204/182.9, 183.2, 299 R, 204/182.8, 180.1

[56] References Cited

U.S. PATENT DOCUMENTS

| | | | |
|---|---|---|---|
| 3,485,736 | 12/1969 | Vesterberg | 204/180 |
| 4,130,470 | 12/1978 | Rosengren et al. | 204/180 |
| 4,243,507 | 1/1981 | Martin et al. | 204/301 |
| 4,290,911 | 9/1981 | Cook et al. | 252/316 |
| 4,312,739 | 1/1982 | Hannson et al. | 204/299 |

OTHER PUBLICATIONS

G. V. Troitsky et al., "Isoelectric Focusing of Proteins Using a pH Gradient Created by a Concentration Gradient of Nonelectrolytes in Solution", *Biochim. Biophys. Acta* 400(1): 24–31 (1975).
G. V. Troitsky and G. Y. Azhitsky, "Highly Stable pH–Gradients Formed by Polyhydroxyl Compounds, Boric Acid and Borates: Theoretical Aspects and Application to Isoelectric Focusing of Proteins, Peptides and Amino Acids", *Journal of Chromatography* 324: 285–297 (1985).
G. V. Troitsky et al., "Isoelectric Focusing in the Boric Acid–Borate Buffer–Mannitol System", *Med. Khim.* 22(2) 282–286 (1976) [*Chem. Abstr.* 84: 176089j].
G. V. Troitsky et al., "Two-Dimensional Electrophoresis of the Products Obtained After Limited Hydrolysis of Human Bloom Serum Albumin Using Isoelectric Focusing in a Borate-Polyol System", *Med Khim* 33(2): 136–138 (1987) [*Chem Abstr.* 106: 210402r].
N. L. Ovchinnikova et al., "Study of Globulins from Cotton Seeds, XXIII. Isoelectrofocusing of 7S Globulin in a Borate-Polyol System", *Khim. Prir. Soedin* (4): 557–578 (1980) [*Chem Abstr.* 93: 181378t].
S. A. Shukun et al., "Protein Separation in pH Gradients Using Free-Flow Electrophoretic Apparatus: 1. The Borate-Mannitol pH Gradients", *Electrophoresis* 6:v 69–74 (1985).
S. A. Shukun et al., "Protein Separation in pH Gradients Using Free-Flow Electrophoretic Apparatus:2. The pH Gradient Formed by the Concentration Gradient of Boric Acid in Solutions of Borax and Mannitol", *Electrophoresis* 6: 75–77 (1985).
Kozulic et al., "Poly-N-Acryloyl-Tris Gels as Anticonvection Media for Electrophoresis and Isoelectric Focusing", *Analytical Biochemistry* 163: 506–512 (1987).
Kozulic et al., "Electrophoresis of DNA Restriction Fragments in Poly-N-Acryloyl-Tris Gels", *Analytical Biochemistry* 170: 478–484 (1988).

*Primary Examiner*—John F. Niebling
*Assistant Examiner*—John S. Starsiak, Jr.
*Attorney, Agent, or Firm*—Haverstock, Garrett & Roberts

[57] ABSTRACT

The present invention provides an improved method for forming pH gradients or other pH functions for use in electrophoresis and isoelectric focusing. It also involves electrophoresis and IEF devices created by such methods, and improved reagents suitable for generating such devices. The method involves (1) chemically affixing or "anchoring," in a concentration gradient or other varying function, selected molecules which form acidic complexes when contacted by certain acidic compounds, and (2) contacting the anchored molecules with a fluid containing a suitable acidic compound. One example of a paired combination of anchored molecules and acid comprises (a) anchored molecules with polyhydroxyl groups and (b) boric acid, borax, and/or other borate constituents. The borate will form acidic complexes with the anchored polyhydroxyl groups, generating pH's which will vary within the device depending on (1) the concentration and type of polyhydroxyl groups that are anchored in the device and (2) the composition and pH of the borate buffer.

28 Claims, No Drawings

METHOD OF GENERATING PH FUNCTIONS IN ELECTROPHORESIS AND ISOELECTRIC FOCUSING

FIELD OF THE INVENTION

This invention is in the fields of electrophoresis, isoelectric focusing, and chemical separation processes (especially protein separation).

BACKGROUND OF THE INVENTION

In general, electrophoresis (EP) is a method of separating chemical substances (such as mixtures of proteins) by passing a mixture through a separation medium. An externally-applied voltage is used to drive the different molecules in the mixture through the separation medium at varying rates, usually in a convection-stabilized path to avoid channeling. Electrophoresis is described in various texts such as *Electrophoresis: Theory, Techniques, and Biochemical and Clinical Applications* by A. T. Andrews (Oxford Univ. Press, 1986) and in various patents classified in Class 204, subclasses 180-190, such as U.S. Pat. Nos. 4,292,154 (Ambler 1981) and 4,579,783 (Ogawa 1986).

In one common type of electrophoresis, the molecules of interest continue to move as long as voltage is applied to the separation medium. To prevent these molecules from being driven all the way through the gel, paper, or other separation medium, a marker compound such as bromphenol blue is usually added to the fluid being processed. When the marker has travelled a certain distance, the voltage is turned off and the separation process stops. The desired molecules, which have collected in relatively small zones, may be removed from the separation medium, or they may be visualized in the matrix by any of a variety of staining techniques.

A variant of electrophoresis, usually referred to as isoelectric focusing (IEF) or electrofocusing, involves passing a mixture through a separation medium which contains, or which may be made to contain, a pH gradient or other pH function. The device or gel has a relatively low pH at one end, while at the other end it has a higher pH. IEF is discussed in various texts such as *Isoelectric Focusing* by P. G. Righetti and J. W. Drysdale (North Holland Publ., Amsterdam, and American Elsevier Publ., New York, 1976).

As commonly used, the term "gradient" implies that there are no abrupt boundaries in a function which is changing. Under that definition, a graph of a pH gradient in an IEF device would be shown as a smooth curve with no sharp points. By contrast, the term "function" is broader; it includes gradients, but it also includes transitions which may contain abrupt changes at the boundary between two zones. It is possible to create pH functions with sharp boundary changes in IEF devices by various processes, such as (1) partially filling an IEF device with a certain substance, creating a gradient within that zone if desired; (2) halting the flow of liquid to the IEF device while the concentration of acid or other compound is increased or decreased to a desired level; and (3) adding more fluid to the IEF device. That will create two or more zones with widely varying pH levels Similarly, any other compound can be added, such as a different monomer which will form a different type of gel. The most commonly used gels are agarose and polyacrylamide.

The charge on a protein or other amphoteric molecule depends on the pH of the ambient solution. At the isoelectric point (pI) for a certain molecule, the net charge on that molecule is zero. At pH's above the pI, the molecule has a negative charge, while at pH's below the pI the molecule has a positive charge. Each different "ampholyte" (amphoteric electrolyte) has a characteristic isoelectric point.

When a mixture of ampholytes is electrophoresed in an IEF system, an anode (positively charged) is placed at the acidic end of the system, and a cathode (negatively charged) is placed at the alkaline end. Each ampholyte which has a net positive charge under the acidic conditions near the anode will be driven away from the anode. As it moves through the IEF system, it will enter zones having less acidity, and its positive charge will decrease. Each ampholyte will stop moving when it reaches its particular isoelectric point, since it no longer has any net charge at that particular pH. This effectively separates the ampholytes, since they have different pI's. The isolated molecules of interest can be removed from the IEF device by various means, or they can be stained or otherwise characterized.

Some types of IEF systems generate pH gradients by means of "carrier ampholytes." These are synthetic ampholytes which often have a significant amount of buffering capacity. When placed in an IEF device, each carrier ampholyte will seek its own isoelectric point. Because of their buffering capacity, many carrier ampholytes will establish a pH plateau rather than a single point. By using a proper mixture of carrier ampholytes, it is possible to generate a relatively smooth pH gradient for a limited period of time. Such mixtures are sold commercially under various trade names, such as Ampholine (sold by LKB-Produkter AB of Bromma, Sweden), Servalyt (sold by Serva Feinbiochemica of Heidelberg, FRG), and Pharmalyte (sold by Pharmacia Fine Chemicals AB, Uppsala, Sweden). The chemistry of ampholyte mixtures is discussed in various references, such as Righetti, supra, and in U.S. Pat. No. 3,485,736 (Vesterberg, 1969).

Carrier ampholytes suffer from various problems and limitations. They tend to be hydrolyzed by the electrodes, and they are relatively expensive. It has also been reported (Righetti, supra, at page 75) that commercially available carrier ampholytes do not perform as well as recycled carrier ampholytes. In addition, carrier ampholytes can interact with the proteins being separated, interfering with the separation process, and they can interfere with some visualization techniques. Carrier ampholytes also suffer from problems such as "cathodic drift" and the "plateau effect," which cause instability of the desired pH gradients.

U.S. Pat. No. 4,130,470 (Rosengren et al, 1978) discloses a method of generating an affixed pH gradient in an IEF device. That method involves the use of chargeable groups (such as carbonic, sulphonic, boric, or phosphonic acids, or amino groups) which are immobilized in the separation medium at a range of concentrations. That system also suffers from several limitations, including: (1) some proteins precipitate and form strong complexes with the charged group of the matrix, especially when aging monomer solutions are used to generate the pH gradient; (2) amino groups in the matrix adhere to untreated glass and other solid materials, making it difficult to remove gels from the devices after focusing, and making recovery of the sample difficult; (3) the reagents needed to prepare IEF media according to Rosengren et al are relatively expensive; (4) pre-manufactured gels normally must be dried and/or kept frozen for shipping and/or storage; and (5) gels made according to the method of Rosengren et al tend to suffer from swelling and endosmosis.

A different method of generating a pH gradient for use in IEF was developed by Troitsky et al, at the Crimean Medical Institute in the USSR. This method is described in *Bull. Exp. Biol. Med.* 75: 118–120 (1973; published in Russian) and in *Biochim. Biophys. Acta* 400: 24–31 (1975; published in English). This method is based on the fact that some borate compounds form acidic complexes with some organic molecules having polyhydroxyl groups (i.e., having more than one OH group; these are often called polyols). Borate-polyol complexes are discussed in, e.g., F. Cotton and G. Wilkinson, *Advanced Inorganic Chemistry*, 2nd ed., Volume 3 (John Wiley, New York, 1965). Based on that knowledge, Troitsky et al created IEF columns with buffer solutions containing borate compounds and gradients of certain polyhydroxyl compounds such as glycerol, mannitol, and sucrose. Those columns were used to perform IEF separation on several mixtures of proteins, such as human or rabbit hemoglobins.

Troitsky et al reported successful results with the specific protein mixtures they used, and they subsequently described several similar experiments using non-anchored polyols in Troitsky and Agitsky, *Isoelectric Focusing of Proteins in Self-Organizing and Artificial pH Gradients*, page 117; published in Russian by Naukova Dumke, Kiev, 1984. However, the systems they described suffer from several limitations. First, the acidic complexes formed by the borate have ionic charges, which causes them to move within the IEF device when voltage is applied. Second, because most polyhydroxyl compounds (such as glycerol and mannitol) are relatively dense, they were loaded into the bottoms of vertical columns. That tended to stabilize the placement of the polyols in the column while it remained vertical; however, it would have interfered with the use of horizontal IEF devices, which are preferred in some situations. In addition, it would be impractical to pre-manufacture and ship IEF devices having gradients generated according to the Troitsky method, or to store them for prolonged periods.

Various other reports of electrophoresis experiments describe the use of borate buffers and/or gels which contain polyhydroxyl compounds, although none use both ingredients in the manner described below. For example, Kozulic et al created gels containing gradients of poly-NAT, the common name for polymerized N-acryloyl-tris(hydroxymethyl)aminomethane. The purpose of generating those concentration gradients was to generate a gradient of pore sizes, so the gels could be used as molecular sieves in electrophoresis, to separate large proteins according to their size. Kozulic et al also used gels containing NAT in uniform concentrations, with no gradients, for IEF separation of proteins using carrier ampholytes. Both sets of experiments are described in M. Kozulic et al, *Analytical Biochemistry* 163: 506–512 (1987). In addition, Kozulic et al used gels having uniform concentrations of NAT to separate nucleic acids, using buffers that are commonly used for nucleic acid separation. One such buffer contain Tris, the common name for tris(hydroxymethyl)aminomethane, and borate. That borate buffer reportedly caused the gels to swell, producing unsatisfactory results. That work is described in B. Kozulic et al, *Analytical Biochemistry* 170: 478–484 (1988).

The object of this invention is to create EP and IEF systems and devices which: (1) can be manufactured using relatively inexpensive reagents; (2) are highly stable while in use, and do not suffer from cathodic drift or plateauing; (3) cause low levels of interaction and interference with proteins and other substances being separated; (4) can be created reliably and precisely by lab technicians with minimal training; (5) can be pre-manufactured in large numbers using automated equipment; (6) can be shipped and stored for prolonged periods without the need for drying or freezing; (7) can be easily removed from holding devices; and (8) can be used under widely varying conditions.

SUMMARY OF THE INVENTION

The present invention provides an improved method for forming pH gradients or other pH functions for use in electrophoresis and isoelectric focusing. It also involves electrophoresis and IEF devices created by such methods, and improved reagents suitable for generating such devices. The method involves (1) chemically affixing or "anchoring," in a concentration gradient or other varying function, selected molecules which form acidic complexes when contacted by certain acidic compounds, and (2) contacting the anchored molecules with a fluid containing a suitable acidic compound. One example of a paired combination of anchored molecules and acid comprises (a) anchored molecules with polyhydroxy groups and (b) boric acid, borax, and/or other borate constituents. The borate will form acidic complexes with the anchored polyhydroxyl groups, generating pH's which will vary within the device depending on (1) the concentration and type of polyhydroxyl groups that are anchored in the device and (2) the composition and pH of the borate buffer.

DETAILED DESCRIPTION OF THE INVENTION

In one preferred embodiment of this invention, an electrophoresis device such as a vertical or slanted glass tube is filled with two monomer solutions A and B. The tube is filled using any suitable gradient-forming method and device, such as a mixing chamber which initially contains solution A, coupled to a reservoir which contains solution B. After the gradient is poured, the concentration of solution A ranges from 100% at the bottom of the tube to 0% at the top; the concentration of B ranges from 0% at the bottom to 100% at the top. By controlling the rate at which solution B is added to the mixing chamber, the gradient can be linear, convex, or concave.

Monomer solution A which can be used in this invention comprises:

(1) a selected polyol derivative as described below, in the form of a monomer which can form a polymeric gel when cross-linked, such as 15% N-acryloyl glucamine (as used herein, concentration percentages indicate weight per volume, such as 15 grams of monomer in 100 milliliters of solution);

(2) a selected polymerization catalyst, such as 0.5% N,N,N',N'-tetramethylethylenediamine;

(3) a selected polymerization initiator, such as 0.1% ammonium persulfate;

(4) if desired, an additional monomer (such as acrylamide) which can form a polymeric gel when cross-linked, but which does not have polyol groups as described below;

(5) a selected cross-linking agent, such as 0.2% BIS (the common name for (N,N'-methylene-bisacrylamide); and (6) an electrophoresis buffer containing a suitable acid or salt which can form molecular complexes with polyhydroxyl groups, such as 20 millimolar (mM) boric acid in water titrated to pH 7.0 by solid tris-(hydroxymethyl)aminomethane.

Monomer solution B comprises:

(1) a monomer such as acrylamide which can form a polymeric gel, but which does not have polyhydroxyl groups as described below, and/or a monomer which contains polyhydroxyl groups, but which is chemically different than the polyhydroxyl-containing monomer of solution A;

(3) a polymerization initiator, a polymerization catalyst, and a cross-linking agent; and (4) an electrophoresis buffer, preferably identical to the buffer contained in monomer solution A.

After the tube has been filled with the gradient of mixtures A and B, the polymerization and cross-linking reactions are initiated by any suitable method, depending on the reagents used. For example, instead of using a peroxide compound such as ammonium persulfate, azo compounds, redox pairs, or radiation sensitive substances such as riboflavin can be used. The result is a polymeric gel which is permeable to water and protein.

As used herein, the term "permeable" includes separation media that are only partially permeable; if a separation medium is permeable to the molecules being separated, it is regarded as "permeable" for the purpose of the claims even though it might be non-permeable to other molecules such as very large proteins or DNA fragments. In addition, the term "permeable" includes fluids, and it includes mixtures of permeable and non-permeable material so long as the mixture taken as a whole is permeable; for example, fluid separation media (which is permeable) can be used in conjunction with capillary tubes or granular particles which, individually, are non-permeable.

In the gel described above, the polyhydroxyl groups are anchored, but the borate molecules and ions are mobile. The borate molecules form non-covalently bound complexes with the anchored polyhydroxyl groups originally contained in monomer solution A. Those complexes, which are acidic, are present at higher concentrations near the bottom of the tube, where there is a higher concentration of polyhydroxyl groups. This causes the pH within the gel to be relatively low (acidic) at the bottom of the tube and progressively higher (more alkaline) farther up the tube.

A solution containing a mixture of proteins, which preferably has been dialyzed against the electrophoresis buffer, is applied to the top of the tube. The tube is subjected to electrophoresis at a suitable voltage, with the cathode (negative charge) at the top and the anode (positive charge) at the bottom.

After a suitable period, typically ranging from 4 to 24 hours for a tube 10 cm long, the voltage is discontinued. The various proteins in the mixture will be separated and arranged in the gel according to their isoelectric points. If desired, the gel can be removed from the device and the desired protein can be removed from the gel by methods such as elution. Alternately, the proteins can be stained or otherwise treated or analyzed using any conventional method.

The chemical substances used to create the separation media of this invention should comprise molecules with at least two types of moieties: (1) moieties, such as polyhydroxyl groups, which can form acidic complexes when contacted with a selected acid, and (2) anchoring groups.

"Polyhydroxyl" refers to molecules having two or more hydroxyl groups. By adding anchoring groups, suitable polyhydroxyl derivatives which form acidic complexes with borate can be formed from various types of sugars, such as glucose, maltose, lactose, etc. Derivatives can also be formed by adding anchoring groups to sugar alcohols such as xylitol, mannitol, glycerol, etc. Suitable derivatives can also be formed from (1) various amino derivatives of polyhydroxyl molecules, such as glucamine, glucosamine, and galactosamine, (2) various carboxyl derivatives of polyhydroxyl molecules, such as glucuronic acid, and (3) derivatives of polyhydroxyl acids, such as lactones and amides.

As used herein, the term "selected acidic compound" refers to a compound which (1) is chosen and used as described herein to generate a pH function in an EP or IEF device, and (2) lowers the pH of a fluid when the compound is added to the fluid, or when it forms complexes with the anchored molecules.

Acidic compounds which are preferred for use in this invention include boric acid ($H_3BO_3$), borate salts, and borax (the common name for $Na_2B_4O_7$). The concentration of borate in the buffer will normally range from less than 1 millimolar (mM), to create separation media having basic pH, up to about 0.3 molar to generate for acidic pH's. The upper limit of borate concentration depends on solubility and conductivity limits. The lower limit depends on the buffering capacity of the fluid.

Boric compounds form complexes with polyhydroxyl molecules as follows:

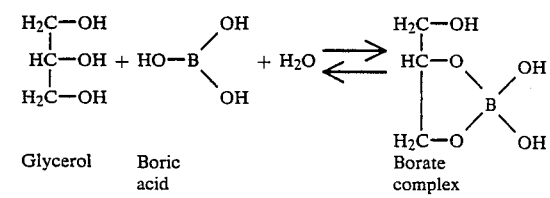

Glycerol   Boric acid                Borate complex

Borate complexes are formed most easily with hydroxyl groups attached to adjacent carbon atoms. Boron can also form complexes with some molecules having hydroxyl groups separated by additional carbon atoms, such as tris(hydroxymethyl)aminomethane and pentaerythritol, and with sugars and sugar derivatives having hydroxyl groups located on opposite sides of the plane of the saccharide ring. Some polyhydroxyl molecules (such as sucrose and polyvinyl alcohol) have a relatively low affinity for boric compounds. For example, Troitsky and Agitsky report the following range of pK's for boric acid complexes with the following polyhydroxyl groups: mannitol, 2.75; sorbitol, 3.64; xylitol, 3.92; galactose, 5.59; glucose, 5.82; glycerol, 6.54; lactose, 6.97; sucrose, 7.26; maltose, 7.76 (Troitsky 1984, supra). It should also be noted that for boric acid alone, the pK is 9.24; this indicates that boric acid is a very weak acid, and borate-polyhydroxyl complexes are more acidic than the acid alone.

Low-affinity polyhydroxyl molecules may be unsuitable for generating steep pH gradients; however, they can be used to generate relatively shallow gradients, which are preferable for separating some mixtures. The pH effects of any particular polyhydroxyl molecule in combination with any particular borate compound can be determined through routine experimentation, and suitable combinations and concentrations can be chosen to create any desired pH gradient or other function.

It is preferable to avoid using polyhydroxyl molecules having two hydroxyl groups bonded to the same carbon atom, to avoid or minimize the formation of aldehydes and other undesired molecules.

As mentioned above, the polyhydroxyl molecule should be either selected or modified so that it contains an "anchoring group." As used herein, "anchoring group" refers to moieties that are used to form covalent bonds between the polyhydroxyl molecule and a chosen substrate. The substrate can be a monomer (such as acrylamide) which can later be converted into a solid or a gel, or the substrate can be a preformed gel or other material (such as paper, plastic, glass, cellulose acetate, a polystyrene resin or derivative, etc.).

Numerous methods and reagents which can be used to anchor organic molecules to substrates are known to those skilled in the art; any such method can be used, provided that it does not destroy the polyhydroxyl groups used to form acidic complexes. For example, if acrylamide is used as the monomer (or if polyacrylamide is used as a pre-formed gel), the anchoring groups can contain unsaturated bonds, such as vinyl, allyl, acryl, or methacryl groups. Alternately, if the substrate contains primary or secondary amine groups, the anchoring groups can comprise lactones, aldehydes, or epoxides. If the substrate contains hydroxyl groups, then the hydroxyl groups of the reagent can be protected before the anchoring reaction, and the anchoring groups can comprise epoxides, lactones, halogen anhydrides, or alkyl halogens; after the anchoring reaction is completed, the polyhydroxyl groups on the reagent can be de-protected.

If the convection-stabilizing material starts out in solid form (such as paper or cellulose acetate), the polyhydroxyl reagent can be made to migrate into it in a gradient or other variable function. For example, if one end of a paper or acetate strip is immersed into a beaker containing a fluid with the polyhydroxyl reagent, the fluid will permeate into and up the strip because of capillary attraction. After a suitable time, the strip is removed from the beaker; it will contain a concentration gradient, with high levels at the bottom and lower levels at the top. The anchoring reaction can then be initiated to immobilize the polyhydroxyl groups in that gradient.

Alternately, a paper or acetate strip or a preformed gel can be placed in contact along its entire length (or any portion thereof) with a fluid containing a gradient of polyhydroxyl reagent. The reagent will permeate into the strip or gel according to that gradient, and it can then be anchored.

If desired, the polyhydroxyl groups can be covalently bound to solid material (such as the surfaces of glass capillary tubes) or to a gel matrix, or they can be otherwise constrained within a matrix (for example, they can be incorporated as part of a viscous fluid, which can be polymerized if desired). The tube or trough can also be filled with granular or fibrous material, capillary tubes, membranes, or other devices to prevent turbulence. After the tube or trough is full, the fluid can remain in liquid form if the separation device is filled with convection stabilizers.

The gels and other devices of this invention can be used in any EP or IEF setting where stable pH gradients are desired, including discontinuous or "disc" electrophoresis (where sharp transitions exist in the pH's of adjacent zones), "continuous flow" electrophoresis (where the flow of the mixture being separated is perpendicular to the pH gradient, causing the mixture to separate into bands which travel in parallel lines through the device for collection in purified form at the outlet), and two-dimensional EP or IEF (where a mixture is separated according to two different characteristics, such as isoelectric point and molecular size).

The EP and IEF systems and devices which can be generated by this method have a number of important advantages over the prior art, including:

(1) they can be manufactured using relatively inexpensive reagents;

(2) they are highly stable while in use, and do not suffer from cathodic drift or plateauing;

(3) they cause very low levels of interaction and interference with proteins and other substances being separated;

(4) they can be created reliably and precisely by lab technicians with minimal training;

(5) matrices with anchored polyhydroxyl groups, but without borate compounds or other acid, can be pre-manufactured in large numbers using automated equipment; they can be shipped and stored for prolonged periods without the need for drying or freezing, and they can be converted into IEF devices with pH gradients merely by adding borate or other suitable acidic compounds;

(6) the separation media of this invention can be easily removed from holding devices; and (7) they can be used under widely varying conditions, in horizontal as well as vertical or tilted modes.

The methods and devices of this invention will allow simpler, less expensive, and more reliable use of electrophoresis and IEF in a variety of situations, including research, pharmaceutical manufacturing, and hormone purification. This invention also will allow IEF to be used in clinical settings, where it is rarely used today because its complexity requires careful preparation of each gel or device and extensive training of technicians.

Numerous equivalents to the specific embodiments described herein can be determined by those skilled in the art, using routine experimentation. Such equivalents are within the scope of the claims.

I claim:

1. A method of generating a pH function for use in electrophoresis or isoelectric focusing, comprising contacting a permeable medium with a selected acidic compound, wherein:
   (a) the permeable medium comprises anchored molecules which form molecular complexes with the selected acidic compound, and
   (b) the anchored molecules are present in different concentrations in different zones within the permeable medium.

2. A method of claim 1 wherein the anchored molecules contain polyhydroxyl groups.

3. A method of claim 1 wherein the acidic compound is selected from the group consisting of boric acid, borate salt, and borax.

4. A method of claim 2 wherein the acidic compound is selected from the group consisting of boric acid, borate salt, and borax.

5. A method of generating a pH function in a permeable medium, comprising the following steps:
   (a) creating a permeable medium containing selected anchored molecules that are present in different concentrations in different zones within the permeable medium; and
   (b) contacting the permeable medium with a selected acidic compound which generates a pH function by forming acidic complexes with the anchored molecules.

6. A method of claim 5 wherein the anchored molecules contain polyhydroxyl groups.

7. A method of claim 5 wherein the acidic compound is selected from the group consisting of boric acid, borate salt, and borax.

8. A method of claim 6 wherein the acidic compound is selected from the group consisting of boric acid, borate salt, and borax.

9. A method of generating a pH function for use in electrophoresis or isoelectric focusing, comprising contacting a convection-stabilized permeable medium with a selected acidic compound, wherein:
   (a) the permeable medium comprises two or more types of anchored polyhydroxyl compounds;
   (b) at least one of the anchored polyhydroxyl compounds is present in different concentrations in different zones within the permeable medium; and
   (c) the acidic compound forms acidic complexes with the anchored polyhydroxyl compounds.

10. A method of claim 9 wherein the acidic compound is selected from the group consisting of boric acid, borate salt, and borax.

11. A method of conducting electrophoresis or isoelectric focusing, comprising the step of contacting a mixture to be separated with a separation device comprising:
   (a) anchored molecules which form molecular complexes with a selected acidic compound, wherein the anchored molecules are present in different concentrations in different zones within the permeable medium; and
   (b) an acidic compound which forms acidic molecular complexes with the anchored molecules.

12. A method of claim 11 wherein the anchored molecules contain polyhydroxyl groups.

13. A method of claim 11 wherein the acidic compound is selected from the group consisting of boric acid, borate salt, and borax.

14. A method of claim 12 wherein the acidic compound is selected from the group consisting of boric acid, borate salt, and borax.

15. A method of creating a separation medium useful for generating an electrophoresis or isoelectric focusing device having a pH function, comprising the step of anchoring, within or on a substrate, selected molecules having polyhydroxyl groups that are capable of forming acidic complexes with borate compounds, wherein the anchored molecules are present in different concentrations in different zones within or on the substrate.

16. A method of creating a separation medium useful for generating an electrophoresis or isoelectric focusing device having a pH function, comprising the step of anchoring, within a permeable medium, selected molecules having polyhydroxyl groups that are capable of forming acidic complexes with borate compounds, wherein the anchored molecules are present in different concentrations in different zones within the permeable medium.

17. A separation medium useful for generating an electrophoresis or isoelectric focusing device having a pH function, comprising molecules having polyhydroxyl groups capable of forming acidic complexes with borate compounds, wherein the molecules have been anchored to a substrate in different concentrations in different zones within or on the substrate.

18. A separation medium useful for electrophoresis or isoelectric focusing, comprising:
   (a) molecules having polyhydroxyl groups capable of forming acidic complexes with borate compounds, wherein the molecules have been anchored to a substrate in different concentrations in different zones within or on the substrate; and,
   (b) one or more borate compounds which form acidic complexes with the molecules of part (a).

19. A separation medium useful for generating an electrophoresis or isoelectric focusing device having a pH function, comprising polyhydroxyl compounds which have been anchored on or within a substrate in different concentrations in different zones on or within the substrate, wherein the polyhydroxyl compounds have been selected for their capability of forming acidic complexes with one or more borate compounds.

20. A separation medium useful for electrophoresis or isoelectric focusing, comprising:
   (a) one or more polyhydroxyl compounds which have been anchored on or within a substrate in different concentrations in different zones on or within the substrate, wherein the polyhydroxyl compounds have been selected for their capability of forming acidic complexes with one or more borate compounds; and,
   (b) one or more borate compounds which form acidic complexes with the molecules of part (a).

21. A separation medium useful for generating an electrophoresis or isoelectric focusing device having a pH function, comprising polyhydroxyl compounds which have been anchored on or within a substrate in different concentrations in different zones on or within the substrate, wherein the polyhydroxyl compounds are selected and used for the purpose of forming acidic complexes with one or more borate compounds.

22. A separation medium useful for electrophoresis or isoelectric focusing, comprising:
   (a) polyhydroxyl compounds which have been anchored on or within a substrate in different concentrations in different zones on or within the substrate, wherein the polyhydroxyl compounds are selected and used for the purpose of forming acidic complexes with one or more borate compounds; and,
   (b) one or more borate compounds which form acidic complexes with the molecules of part (a).

23. A separation medium useful for generating an electrophoresis or isoelectric focusing device having a pH function, comprising molecules having polyhydroxyl groups capable of forming acidic complexes with borate compounds, wherein the molecules have been anchored to a permeable medium in different concentrations in different zones within or on the permeable medium.

24. A separation medium useful for electrophoresis or isoelectric focusing, comprising:
   (a) molecules having polyhydroxyl groups capable of forming acidic complexes with borate compounds, wherein the molecules have been anchored to a permeable medium in different concentrations in different zones within or on the permeable medium; and, (b) one or more borate compounds which form acidic complexes with the molecules of part (a).

25. A separation medium useful for generating an electrophoresis or isoelectric focusing device having a pH function, comprising polyhydroxyl compounds which have been anchored on or within a permeable medium in different concentrations in different zones on or within the permeable medium, wherein the polyhydroxyl compounds have been selected for their capability of forming acidic complexes with one or more borate compounds.

26. A separation medium useful for electrophoresis or isoelectric focusing, comprising:
    (a) one or more polyhydroxyl compounds which have been anchored on or within a permeable medium in different concentrations in different zones on or within the permeable medium, wherein the polyhydroxyl compounds have been selected for their capability of forming acidic complexes with one or more borate compounds; and,
    (b) one or more borate compounds which form acidic complexes with the molecules of part (a).

27. A separation medium useful for generating an electrophoresis or isoelectric focusing device having a pH function, comprising polyhydroxyl compounds which have been anchored on or within a permeable medium in different concentrations in different zones on or within the permeable medium, wherein the polyhydroxyl compounds are selected and used for the purpose of forming acidic complexes with one or more borate compounds.

28. A separation medium useful for electrophoresis or isoelectric focusing, comprising:
    (a) polyhydroxyl compounds which have been anchored on or within a permeable medium in different concentrations in different zones on or within the permeable medium, wherein the polyhydroxyl compounds are selected and used for the purpose of forming acidic complexes with one or more borate compounds; and,
    (b) one or more borate compounds which form acidic complexes with the molecules of part (a).

* * * * *